United States Patent [19]
Finn

[11] Patent Number: 5,215,921
[45] Date of Patent: Jun. 1, 1993

[54] WATER AND AIR MANIFOLD SYSTEM

[75] Inventor: Larry J. Finn, Gladewater, Tex.

[73] Assignee: Bedminster Bioconversion Corporation, Cherry Hill, N.J.

[21] Appl. No.: 783,549

[22] Filed: Oct. 28, 1991

[51] Int. Cl.[5] .......................... C12M 1/10; C12M 1/04
[52] U.S. Cl. ..................................... 435/312; 435/313;
71/9; 71/12; 422/184; 239/416.5; 239/423
[58] Field of Search ..................... 239/416.5, 423, 424;
366/345, 346; 71/9, 12, 14; 435/287, 312, 313,
315, 819; 422/184, 209

[56] References Cited

U.S. PATENT DOCUMENTS

| | | | |
|---|---|---|---|
| 3,041,148 | 6/1962 | Ballantyne et al. | 435/313 |
| 3,138,447 | 6/1964 | Eweson | 71/9 |
| 3,245,759 | 4/1966 | Eweson | 71/9 |
| 3,407,121 | 10/1968 | LeSeelleur et al. | 435/313 |
| 3,676,074 | 7/1972 | Shibayama et al. | 71/9 |
| 3,756,784 | 9/1973 | Pittwood | 71/9 |
| 4,666,854 | 5/1987 | Suguira | 435/313 |
| 5,055,744 | 9/1992 | Petersen | 71/9 |

FOREIGN PATENT DOCUMENTS 3626903 2/1988 Fed. Rep. of Germany ...... 435/315

Primary Examiner—Robert J. Warden
Assistant Examiner—T. A. Trembley
Attorney, Agent, or Firm—Stanley H. Zeyher

[57] ABSTRACT

A water manifold and air supply system for use with a multi-compartment rotating drum apparatus for the fermentation of natural organic material which provides for selective injection of air and predetermined amounts of water into compartments of the drum during its rotation which system includes an air supply conduit concentrically aligned with the rotational axis of the drum, a first water-conduit section fixedly secured to the rotating drum, a second water-conduit section concentric with the rotational axis of the drum residing within the air supply conduit and connected to the first section through a water-tight seal, the two water-conduit sections and air supply conduit being respectively connected to stationary water-supply and air-supply means by swivel joints.

3 Claims, 4 Drawing Sheets

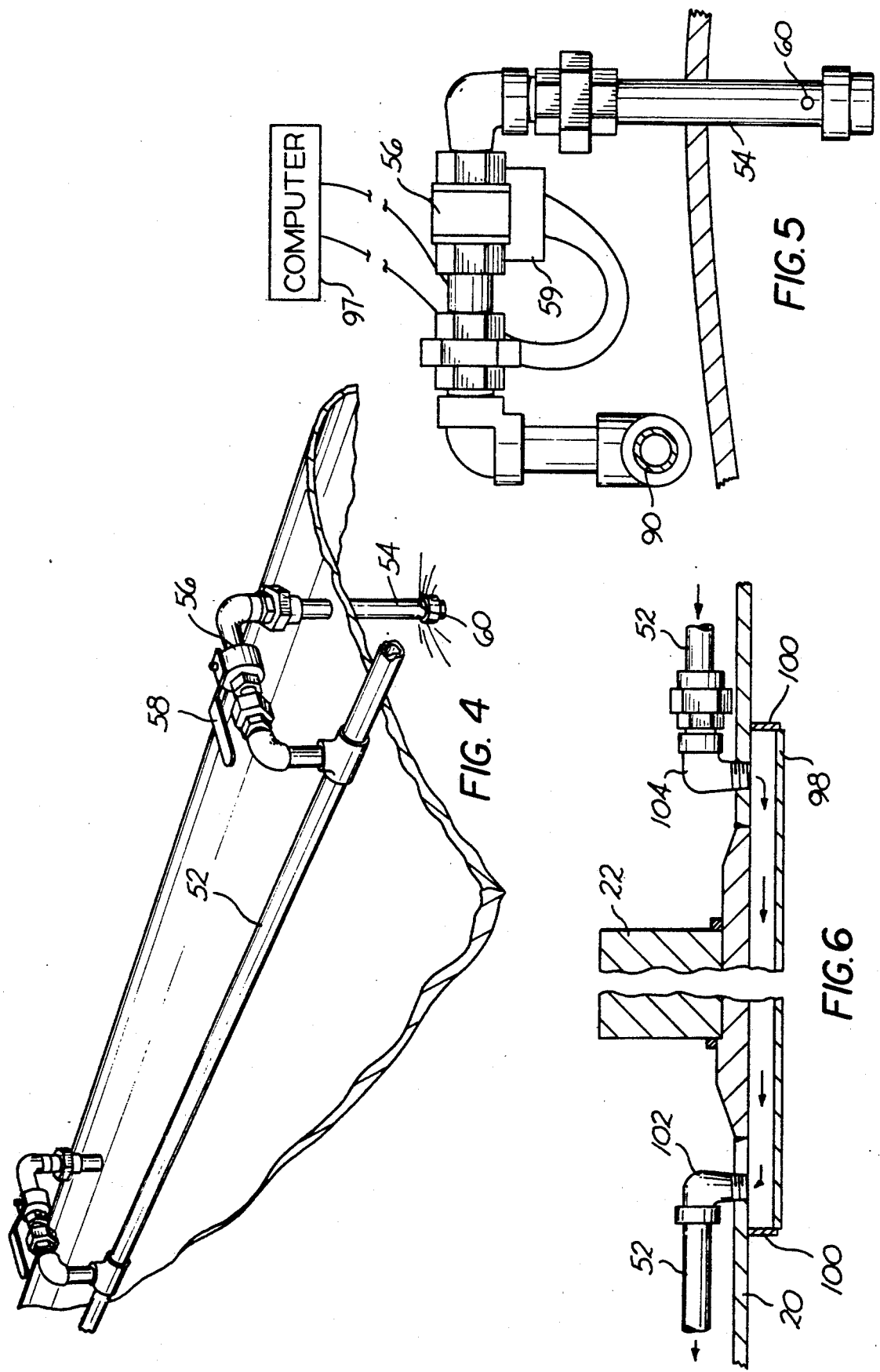

WATER AND AIR MANIFOLD SYSTEM

FIELD OF THE INVENTION

This invention relates broadly to apparatus for making organic fertilizer from organic waste material, sometimes referred to as compost, and more particularly to an improved humidifying and air-supply system for use in connection with such apparatus.

BACKGROUND OF THE INVENTION

Prior art systems for achieving composting of solid waste and sewage sludge typically employ one or more multi-stage digesters in which material being treated undergoes staged microbial decomposition. The conventional digester is divided into two or more compartments or stages and during material processing is rotated while air is circulated through the digester at controlled rates under predetermined conditions in a flow direction counter to the material flow. The climate in each stage is maintained to achieve the optimum development of the type and species of microorganism predominant in that stage. Spent air is vented from the digester to the atmosphere and water vapor added, as needed. To maintain optimum climatic conditions in each of the operating stages temperatures are kept below 150 degrees F. to ensure the maximum rate of composting. Typical of such prior art systems and methodology of operation are those set out and described in U.S. Pat. Nos. 3,245,759 and 3,138,447 assigned to the assignee of the present invention, the teachings of which are hereby incorporated by reference.

The method and apparatus for manufacture of compost described in those patents is designed to produce aerobic decomposition of organic waste materials by maintaining within the apparatus in which the method is carried out, conditions suitable for optimum propagation of the different types of aerobic bacteria on which such decomposition depends. The apparatus comprises a digester in the form of a cylindrical drum mounted for rotation on an axis which is slightly declined towards the discharge end relative to the horizontal. The interior of the digester is divided into a series of compartments or chambers by a plurality of transverse partitions spaced along the axis of rotation. Each partition is provided with transfer buckets which are selectively opened and which when opened, transfer material from compartment to compartment from the higher to the lower end of the drum, the raw waste organic material being fed into the digester at the higher end and partially cured compost being withdrawn at the lower end.

The co-composting technology to which the present invention has particular application embodies a fermentation reactor which is employed to accelerate the microbial conversion of solid waste and sewage sludge into a high quality compost. The process has the ability to compost municipal solid waste and sewage together hence the term co-composting, thereby addressing the two principal waste management problems communities will face in the next few decades.

An important step in the overall composting process is the maintenance in each of the operating stages of the process of proper humidity conditions to insure optimal microbial growth.

Prior art techniques for maintaining proper moisture content of the entrained mass within the various compartments of the rotating digester drum were to stop the rotation of the drum and to spray water on the compost through open manways or sampling ports.

I have discovered that by installing a water manifold system fixedly secured to the drum with multiple spray nozzles communicating with each compartment and by providing the manifold with a rotating connection concentric with the rotational axis of the drum it is possible to provide for water additions to the entrained compost mass without stopping the digester or impairing the ongoing biological process. Furthermore, each spray nozzle that directs water into an associated composting compartment has its own shut-off valve making it possible to selectively direct water only to that section of the system where additional water is needed.

An alternative embodiment of the invention is one in which the dual functions of providing process air and of humidifying the entrained mass undergoing composting are combined into a composite feed system utilizing concentric conduits aligned with the rotational axis of the digester drum. One section of the air conduit feeds directly into and is attached to the discharge end of the digester at its center line. A second section of the air conduit is stationary and interconnects with the first section through an air-tight rotating joint. The section of the water manifold system aligned with the rotational axis of the drum is concentric with and disposed within the air conduit. This construction permits both of these critical functions to be carried out in a confined area with minimal space requirements.

BRIEF DESCRIPTION OF THE DRAWINGS

For the purpose of illustrating the invention, there is shown in the drawings forms which are presently preferred; it being understood, however, that this invention is not limited to the precise arrangements and instrumentalities shown.

FIG. 4 is a partially sectioned isometric view of the water piping and cylinder injection points of the water manifold system.

FIG. 5 illustrates alternative means for effecting valve control of the water injection system.

FIG. 6 is a detail of the water-line construction for bypassing the drum tires and girth gears.

DETAILED DESCRIPTION OF THE INVENTION

Figure 1:
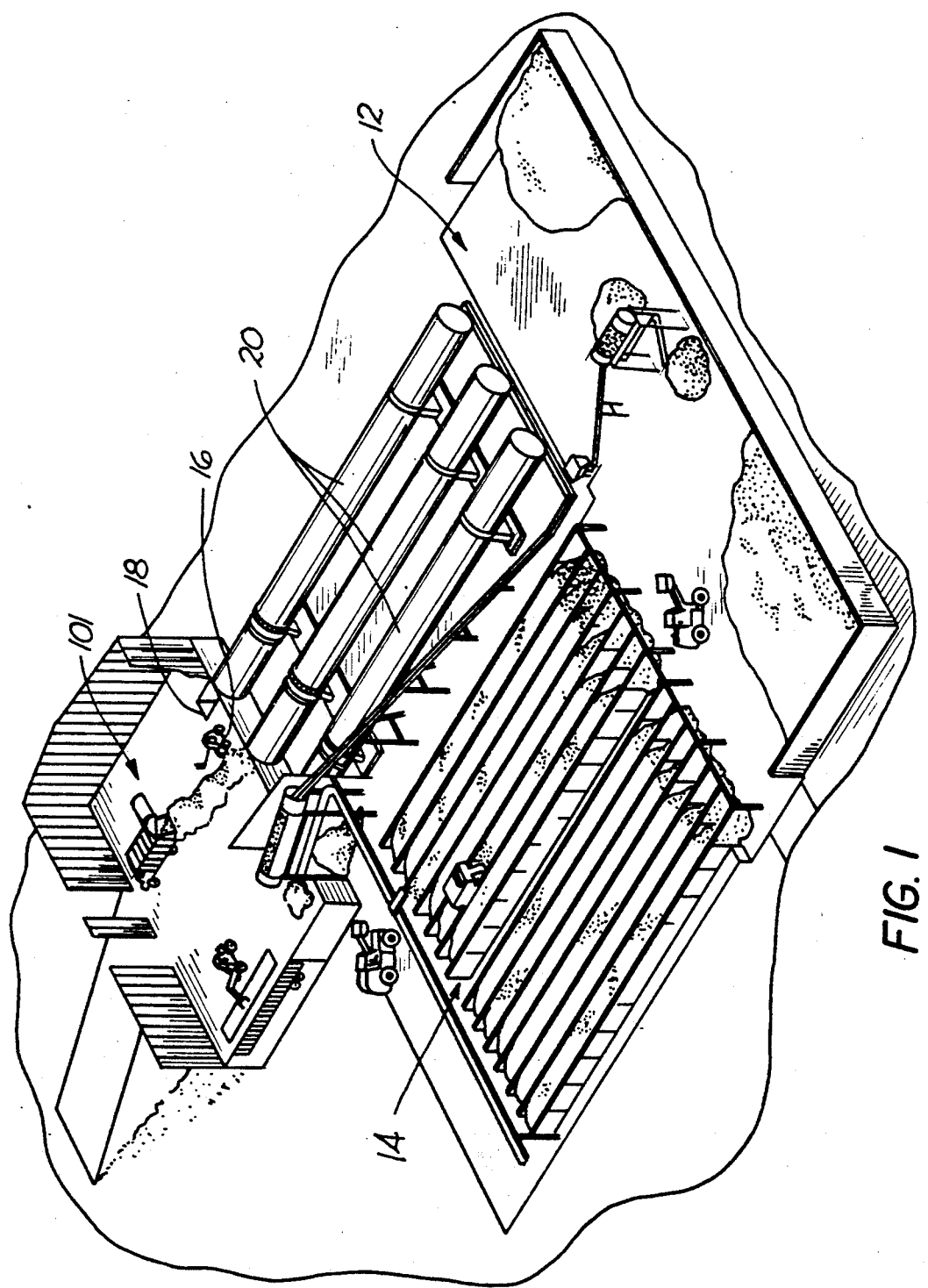
FIG. 1 is an isometric overview of a composting facility depicting a rotating multi-compartment digester drum system for the fermentation of natural organic material.

Referring now to the drawings and more particularly to FIG. 1 thereof, there is shown a composting facility comprised of three major areas, the tipping area 10, a processing area 12, and an aeration or curing area 14. The tipping area floor is where the solid waste is dumped and sorted. Unacceptable waste, for example, white goods, car batteries, tires, large pieces of wood, etc., is rejected and sent to a landfill. The acceptable waste is then moved by means of an end loader 16 from the tipping floor into ram pits 18 positioned at the entry of the digesters 20. Waste is loaded directly into the digester drum by means of an hydraulic loading ram. Sewage sludge delivered to the plant is stored in a liquid sludge tank where it is pumped by liquid sludge pumps directly into the digesters 20 as needed to maintain the proper carbon/nitrogen ratio essential to efficient composting. The material is processed through the digester for a period of three days. The digester is typically divided internally into three fermentation chambers or stages by means of internal partitions. Material is discharged from the digester after approximately three days of residence time.

Essential to this stage of the process is the maintenance of proper humidity conditions for optimal microbial activity. It is to this phase of the process to which the present invention is directed. The various fermentation stages each require different degrees of aeration and have different temperatures and carbon dioxide concentrations. By controlling these parameters of operation the entire process can be conducted and controlled. It is important also that in the parts of the digester where maximum microbic activity is desired that the air supply consists of not fresh air from the atmosphere but of air similar to the kind found in fertile soil, which is saturated with moisture and contains from ten to fifty times as much carbon dioxide as does atmospheric air. Such air becomes available in the process through the microbic activities and can be distributed as required. With moisture the carbon dioxide forms carbonic acid, which aids in rendering the organic wastes assimilable to the microorganisms in the decomposing mass, just as happens in fertile soil.

The microbic developments in the process are caused by aerobic and facultative aerobic fungi, bacteria, and actinomycetes. The exact sequence of these various activities in composting varies considerably depending on slight changes in materials processed, moisture, and pH conditions.

Figure 2:
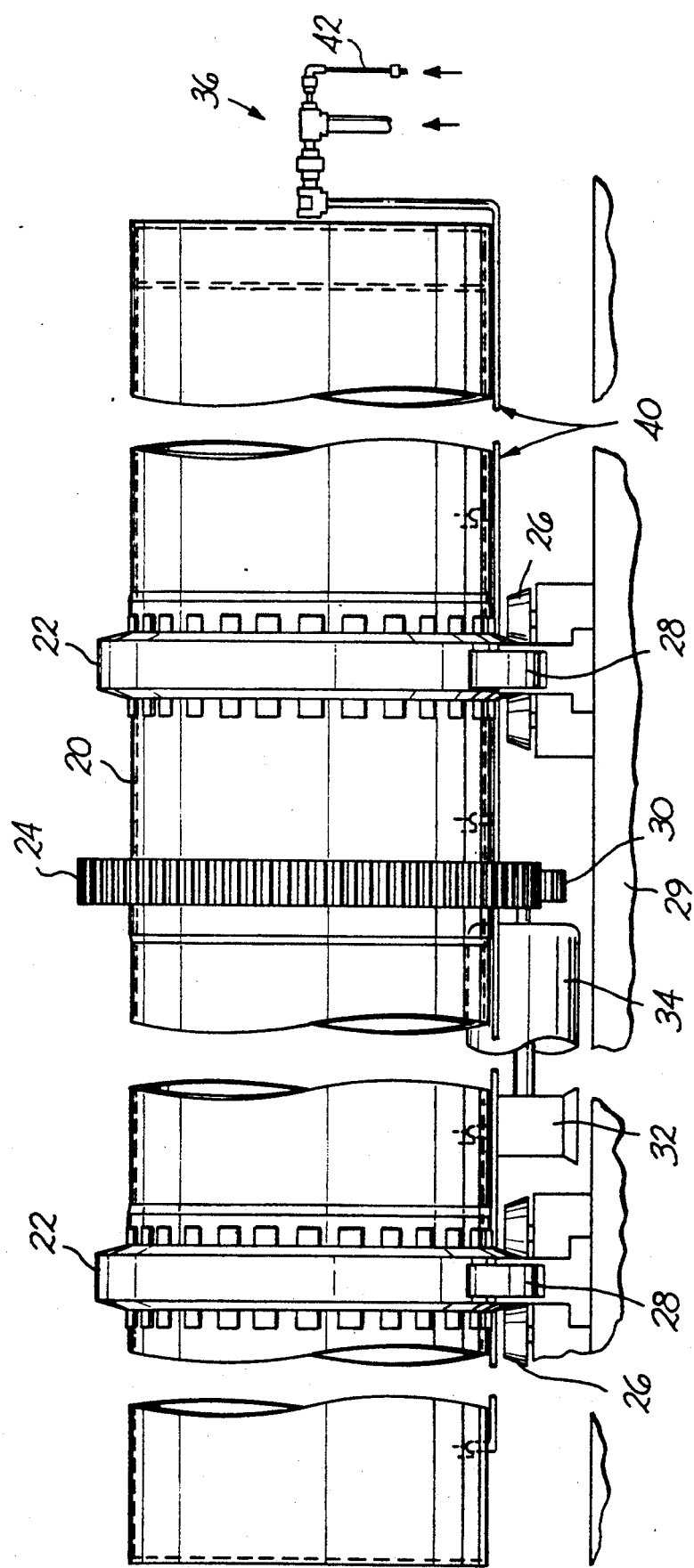
FIG. 2 is an elevational view showing details of the digester drum and water manifold system comprising the present invention.

As seen in FIG. 2, the process is carried out in a rotating digester which is supported on two approximately 20" wide × 14' diameter cast steel tires 22 and one 216 tooth, approximately 21" wide, spring mounted girth gear 24. Each tire rolls over two thrust rollers 26 and two forged steel trunnion rollers 28 (only one of which can be seen for each tire in FIG. 2) all mounted on a fabricated steel trunnion base 29. The girth gear, is engaged by a steel pinion gear 30.

The digester is rotated clockwise by means of a 150-200 horsepower, variable speed high efficiency electric motor 32 coupled to a pinion gear reducer 34. The speed is maintained at approximately 20 revolutions per hour during normal operating conditions and increased to approximately 30 to 40 rph during the unloading and transfer period.

Figure 3:
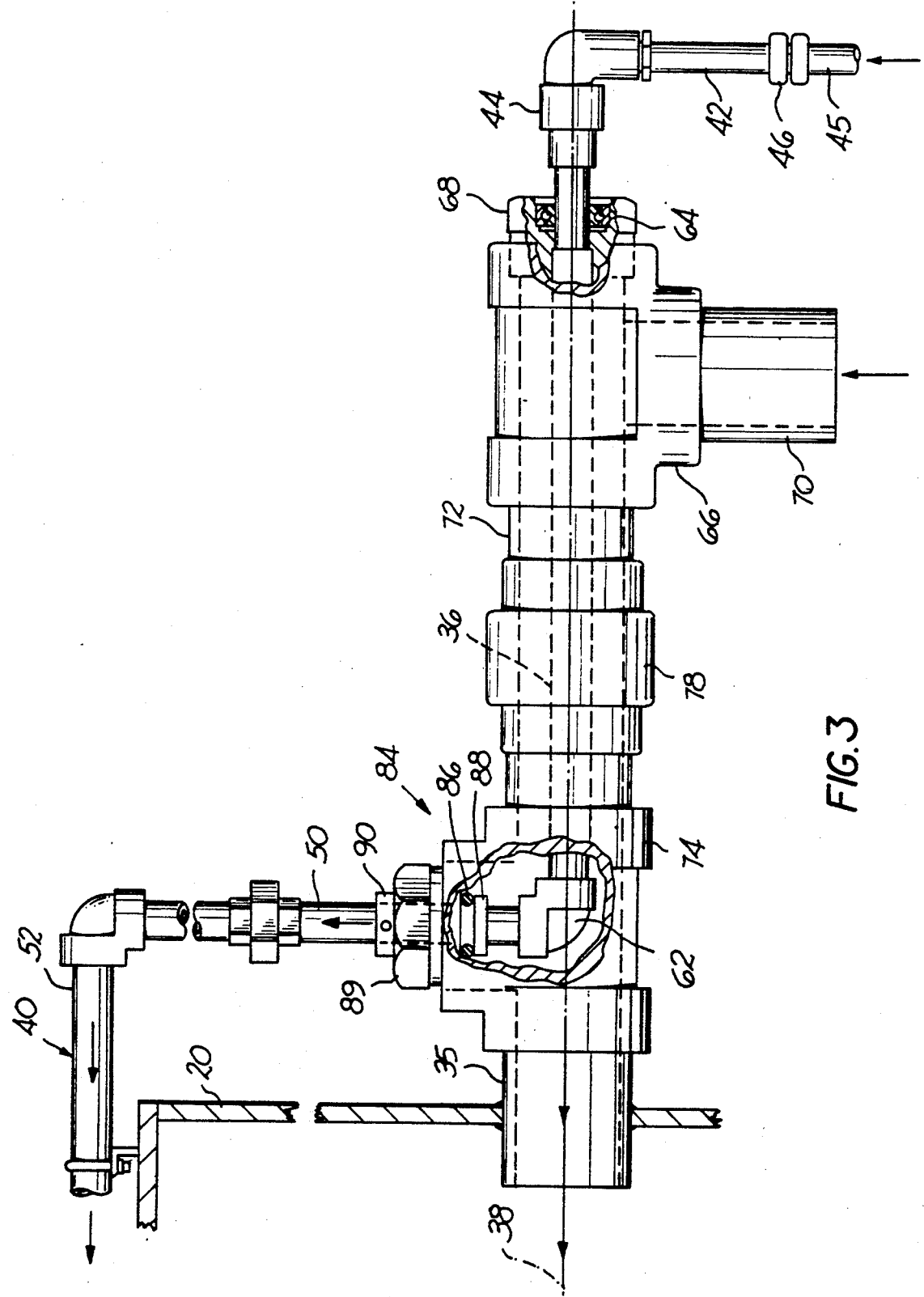
FIG. 3 is a detailed layout of the composite air and water piping system comprising an alternative embodiment of the subject invention.

FIG. 2 is an elevational view showing details of the digester drum and attached water manifold and air supply system. As seen in that Figure and in FIG. 3, the water manifold system, which resides internally of the air conduit 35, comprises a first section 36 disposed concentrically with the rotational axis 38 of the digester drum 20. A second section 40 of the manifold system is secured to the drum for rotation therewith. The first section is connected to a stationary water supply conduit 42 through a swivel or universal joint 44, as best seen in FIG. 3. This arrangement permits relative movement between the stationary and rotating parts of the system.

Water is fed to the water manifold system by means of a hose connection 45 secured to adapter 46. The water is fed through pipes 36, 50, and 52 to spray nozzles 54. As seen in FIG. 4, each spray nozzle has its own shut off valve 56. This valve can be controlled manually by means of lever 58 or, for example, by electronically operated solenoids 59 as seen in FIG. 5. Water is injected into the fermentation chamber as needed through the spray nozzle or capped pipe 54 the internally disposed end of which is provided with ⅜" holes 60 spaced 120 degrees apart.

Referring again to FIG. 3, the detailed structure of the manifold system which is aligned concentric with the rotational axis of the drum, as viewed from left to right in that Figure, consists of a series of galvanized pipe sections comprising "L" section 62 and pipe 36, 24" long threaded at both ends. One end of the pipe is secured to the "L" section 62 and the other end to a low pressure swivel joint 44. The swivel joint in turn is connected to threaded pipe 42 to which is secured the hose adapter 46. This part of the manifold system is supported by a ball bearing 64 mounted on a necked-down, machined surface of pipe 36. The ball bearing is secured to "T" element 66 by pipe plug 68, the "T" being threadably connected to the stationary air input pipe section 70.

As previously noted, the first section of the water manifold system for a multistage digester resides within the air conduit system. The air conduit system is comprised of threaded pipe sections 72 connected at their outer ends to T-sections 74 and 66 and interconnected at their inner ends through swivel joint 78. Pipe section 35 is fixedly secured to the discharge end of digester drum 20. The radially extending section 50 of the water conduit system is connected to the air conduit through a water tight connection 84 comprised of "O" ring 86 interposed between collar 88 and pipe plug 89. The pipe plug is secured in position by collar 90.

As seen in FIG. 4, water flows through pipes 50, 52 to the various spray heads or nozzles 54, each of which is controlled by its own shut off valve 56. The valves are operated either manually by levers 58 or electronically through computer programmed solenoids 96 as seen diagrammatically in FIG. 5. For convenience the computer 97 can be located at a remote control station.

FIG. 6 illustrates one constructional technique for shutting the water line around the tires and girth gear. As illustrated in that Figure a triangular shaped plate 98 is secured to the undersurface of drum 20 as by welding, the ends of which are sealed by triangular end plates 100. The cavity defined by this arrangement is interconnected to the externally located water pipe 52 through "L" connectors 102 and 104.

By means of this composite air/water system the moisture and oxygen content of the composting mass is accurately and efficiently controlled resulting in reduced processing time and an improved end product.

I claim:

1. In a rotating, multi-compartment digester drum for the fermentation of natural organic material, the improvement comprising: a composite air and water piping system for concurrent injection of air and water into drum compartments during drum rotation which system comprises an air conduit and residing therein a two ended first-water conduit section, each of which are in concentric alignment with the rotational axis of said rotating, multi-compartment digester drum, said water piping system having a second conduit section one part of which is fixedly secured to one end of said first water conduit section and an opposite end of which is secured to an external surface of said rotating, multi-compartment digester drum for rotation therewith, the other end of said first water conduit section being connected to a stationary water supply line through a rotating joint, and said air conduit having one end fixedly secured to said rotating, multi-compartment digester drum for rotation therewith and connected at its opposite end to a stationary air supply means through a rotating joint.

2. In a rotating, multi-compartment digester drum for the fermentation of natural organic material, the improvement comprising: an air conduit having two ends, one end of which is fixedly secured to said rotating, multi-compartment digester drum in concentric alignment with its rotational axis and the other end of which is connected to an air supply means via a rotating air-tight joint; water conduit means for selectively injecting predetermined quantities of water into individual ones of said compartments during rotation of the rotating, multi-compartment digester drum, said water conduit means including a first water conduit section having two ends residing within said air conduit and in concentric alignment with the rotational axis of the rotating, multi-compartment digester drum and a second water conduit section, one part of which is fixedly secured to an external surface of the rotating, multi-compartment digester drum and another part of which is connected to one end of said first water conduit section through a water and air-tight connection and said first water conduit section having its other end connected to a stationary water supply conduit through a rotating, water-tight joint.

3. The improvement set out in claim 2 wherein a series of spray nozzles are connected to said second water conduit section and disposed along the surface of the drum and in fluid communication with individual rotating, multi-compartment digester drum compartments and including means for selectively activating individual ones of said spray nozzles to effect selective injection of water into one or another of said compartments.

* * * * *